(12) United States Patent
Durgin et al.

(10) Patent No.: US 6,752,806 B2
(45) Date of Patent: Jun. 22, 2004

(54) UNROLLABLE TIP FOR A CATHETER

(75) Inventors: Russell Francis Durgin, Attleboro, MA (US); Stephen F. Moreci, Hopedale, MA (US); William Stahley, Andover, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 53 days.

(21) Appl. No.: 10/109,635

(22) Filed: Apr. 1, 2002

(65) Prior Publication Data

US 2002/0111623 A1 Aug. 15, 2002

Related U.S. Application Data

(60) Division of application No. 09/499,310, filed on Feb. 7, 2000, now Pat. No. 6,432,104, which is a continuation-in-part of application No. 09/060,780, filed on Apr. 15, 1998, now Pat. No. 6,325,800.

(51) Int. Cl.[7] .............................................. A61B 18/18
(52) U.S. Cl. .............................. 606/45; 606/41; 606/48
(58) Field of Search ............................. 606/32, 39, 40, 606/41, 45, 48, 49, 50

(56) References Cited

U.S. PATENT DOCUMENTS

| | | |
|---|---|---|
| 4,976,711 A | 12/1990 | Parins et al. |
| 5,007,908 A | 4/1991 | Rydell |
| 5,330,470 A | 7/1994 | Hagen |
| 5,336,222 A | 8/1994 | Durgin, Jr. et al. |
| 5,342,357 A | 8/1994 | Nardella |
| 5,391,200 A | 2/1995 | KenKnight et al. |
| 5,403,311 A | 4/1995 | Abele et al. |
| 5,437,662 A | 8/1995 | Nardella |
| 5,441,499 A | 8/1995 | Fritzsch |
| 5,460,629 A | 10/1995 | Shlain et al. |
| 5,496,314 A | 3/1996 | Eggers |
| 5,556,397 A | 9/1996 | Long et al. |
| 5,562,703 A | 10/1996 | Desai |
| 5,672,173 A | 9/1997 | Gough et al. |
| 5,810,764 A | 9/1998 | Eggers et al. |
| 5,904,711 A | 5/1999 | Flom et al. |
| 5,997,534 A | 12/1999 | Tu et al. |
| 6,029,091 A | 2/2000 | de la Rama et al. |
| 6,080,152 A | 6/2000 | Nardella et al. |

FOREIGN PATENT DOCUMENTS

| | | | |
|---|---|---|---|
| EP | 0 779 059 | 3/1995 | |
| EP | 0779059 A1 * | 6/1997 | ........... A61B/5/042 |
| WO | WO 96/00042 | 1/1996 | |

* cited by examiner

*Primary Examiner*—Rosiland K. Rollins
(74) *Attorney, Agent, or Firm*—Kenyon & Kenyon

(57) ABSTRACT

An integrated catheter assembly for enabling diverse endoscopic in situ therapies. The assembly includes a catheter with an irrigation fluid lumen, a distal electrode tip portion that acts as a hemostat, and a cutting wire for making incisions in or ablating tissue. A cutting wire hub provides a sealing entrance for a cutting wire. An operator enables the physician to displace the cutting wire between extended and retracted positions. The cutting wire and electrode are electrically isolated. In addition, the catheter assembly may include a planar tip which, when extended outside the distal end of the assembly, assumes a substantially flat unbiased configuration for use. The apparatus of the present invention allows the physician to make incisions in or ablate tissue using electrosurgery, irrigate tissue, and cauterize or coagulate tissue without having to remove the apparatus from the working channel of the endoscope.

10 Claims, 9 Drawing Sheets

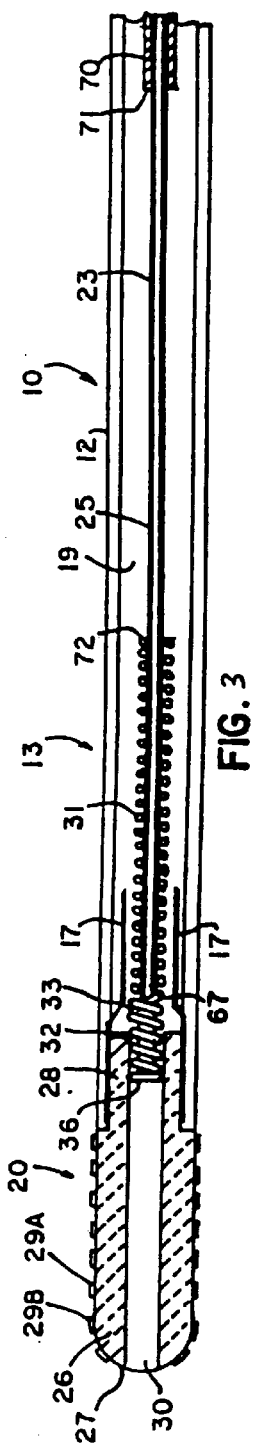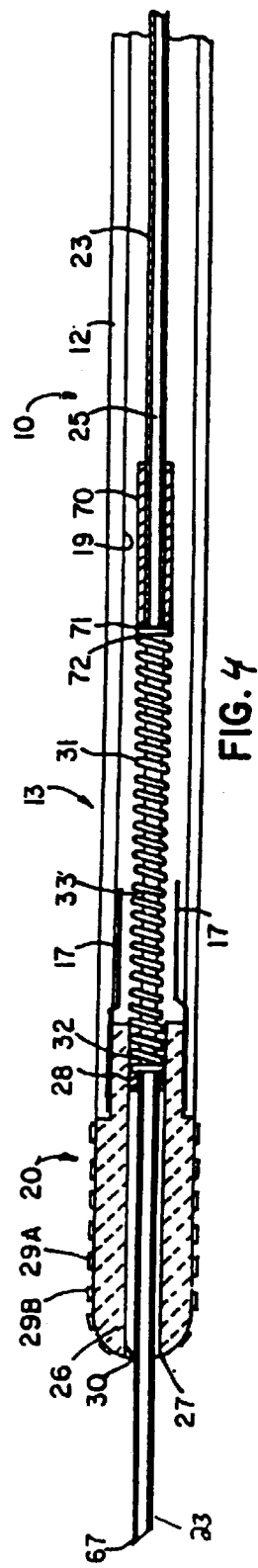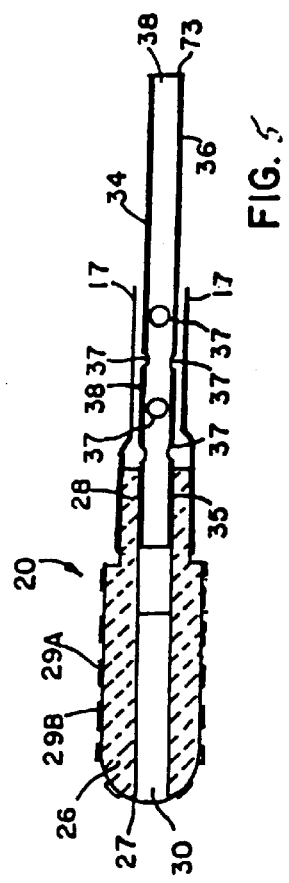

UNROLLABLE TIP FOR A CATHETER

REFERENCE TO RELATED APPLICATIONS

This application is a divisional of application Ser. No. 09/499,310 filed Feb. 7, 2000 now U.S. Pat. No. 6,432,104, which is a Continuation-in-part of application Ser. No. 09/060,780 filed Apr. 15, 1998 now U.S. Pat. No. 6,325,800, which is included herein in its entirety by reference thereto.

FIELD OF THE INVENTION

This invention generally relates to electro-surgery, electro-cauterization and electro-coagulation of tissue in the body in combination with other forms of therapy using catheters. Specifically, this invention relates to an apparatus for performing electrosurgery, electrocauterization and electrocoagulation of tissue through a working channel of an endoscope.

BACKGROUND OF THE INVENTION

Numerous medical procedures involve making an incision in body tissue and controlling any consequent bleeding. When performing these procedures, it is very important to minimize both tissue trauma during incision and the time required to stop internal bleeding. Minimally invasive or least invasive surgical techniques, such as laparoscopic, endoscopic, or arthroscopic techniques, are often used because body tissue is usually traumatized less by those techniques than by more invasive conventional techniques. Electrosurgical methodologies, often used in conjunction with the minimally or least invasive techniques, allow the making of an incision and the stopping or stemming of bleeding with less attendant tissue trauma and greater control than do conventional modalities.

A physician has several medical instruments in his or her armamentarium for making an incision and stemming consequent bleeding. In accordance with one modality that is particularly suited for application in the gastrointestinal tract, a physician initially positions a flexible endoscope in the patient with its distal end proximate to an incision site, and inserts a device for making an incision through a working channel of the endoscope to the incision site. The physician can also insert an irrigator through a working channel in the endoscope to clear the area by administering water or saline solution as a precursor to any attempts to make an incision or stop bleeding.

If the instrument being used for irrigation is like the Gold Probe™ hemostat manufactured by Boston Scientific Corporation, the assignee of this invention, the physician can then cauterize a bleeding vessel using a distally positioned hemostat. Such instruments are constructed to be employed through a working channel of an endoscope to seal potential bleeding sites as in the gastrointestinal tract. Alternatively, the physician can retract the irrigating catheter and insert an elongated needle through the endoscope to inject a vaso-constrictor into the vessel to slow hemorrhaging. Then the physician can remove the elongated needle and reinsert the hemostat to finish the operation.

Some hemostats use mono-electropolar electrodes in which one electrode is carried by a catheter to a site while the other electrode is an exterior ground plate placed in or on a patient. The above-mentioned Gold Probe™ hemostat is an example of a device that supplies a suitable current density and wave form of radio frequency energy to perform electro-coagulation or electro-cauterization. It utilizes a catheter with a bipolar electrode assembly located on a flexible shaft formed of a ceramic cylinder having a hemispherical end. The ceramic tip includes a pair of spaced gold spiral electrodes applied to its cylindrical surface and domed end. RF energy applied to the electrodes produces a current through adjacent tissue that heats and cauterizes the hemorrhaging vessel which is contacted by the tip of the catheter.

Physicians often use different catheters to perform different functions. For example, physicians will often use one catheter to make an incision and another to perform hemostasis and irrigation. The exchange of catheters to provide different functions extends the time to complete therapy, increases the risk to the patient and also increases patient discomfort. Consequently, physicians have to weigh the time, complexity and benefits of interchanging single or dual purpose catheters to change treatment modalities against whatever disadvantage may result by working with a single catheter.

U.S. Pat. No. 5,336,222, the contents of which are incorporated herein, discloses an integrated catheter assembly for enabling diverse in situ therapies which includes a catheter with an irrigation fluid lumen, a distal tip portion that acts as a hemostat and a needle for injection therapy.

SUMMARY OF THE INVENTION

In accordance with this invention, an integrated catheter assembly that enables a physician to utilize diverse in situ therapy modalities at selected tissue sites includes a catheter, an electrode tip and an electrode cutting wire. A lumen extends from a proximal end to a distal end of the catheter structure to provide a passage from a location externally of the patient to the tissue being treated. The bipolar electrode structure attaches to the distal end of the catheter structure and provides hemostatic therapy to selected tissue.

The electrode structure additionally has a central lumen aligned with the catheter lumen for enabling the transfer of irrigation fluids to tissue being treated. The cutting wire structure is electrically isolated from the electrode tip and extends from a proximal end externally of the patient through the lumens in the catheter and the electrode structure for axially displacement relative to the catheter and electrode structures. The cutting wire can be extended distally beyond and can be retracted proximally of a distal end surface of the electrode tip.

In an exemplary embodiment of a catheter assembly according to the present invention, a distal end of the cutting wire includes a substantially planar tip. The planar tip may be formed to achieve both a retracted, substantially circular configuration for insertion through an endoscope and for insertion of the endoscope through a lumen, and an extended, substantially planar configuration for use. The planar tip may further include bipolar circuitry on at least one face.

BRIEF DESCRIPTION OF THE DRAWINGS

The various objects, advantages and novel features of this invention will be more fully apparent from a reading of the following detailed description in conjunction with the accompanying drawings in which like reference numerals refer to like parts, and in which:

FIG. 3 is a side view, partially in section, showing in detail the distal end portion of the apparatus in FIG. 2 including the bipolar electrode assembly in which the cutting wire is retracted.

FIG. 4 is a side view, partially in section, showing in detail the distal end portion of the apparatus in FIG. 2 in which the cutting wire is extended.

FIG. 5 depicts a preferred tip structure that can be substituted for the bipolar electrode assembly shown in FIGS. 3 and 4.

DETAILED DESCRIPTION OF THE INVENTION

Figure 1:
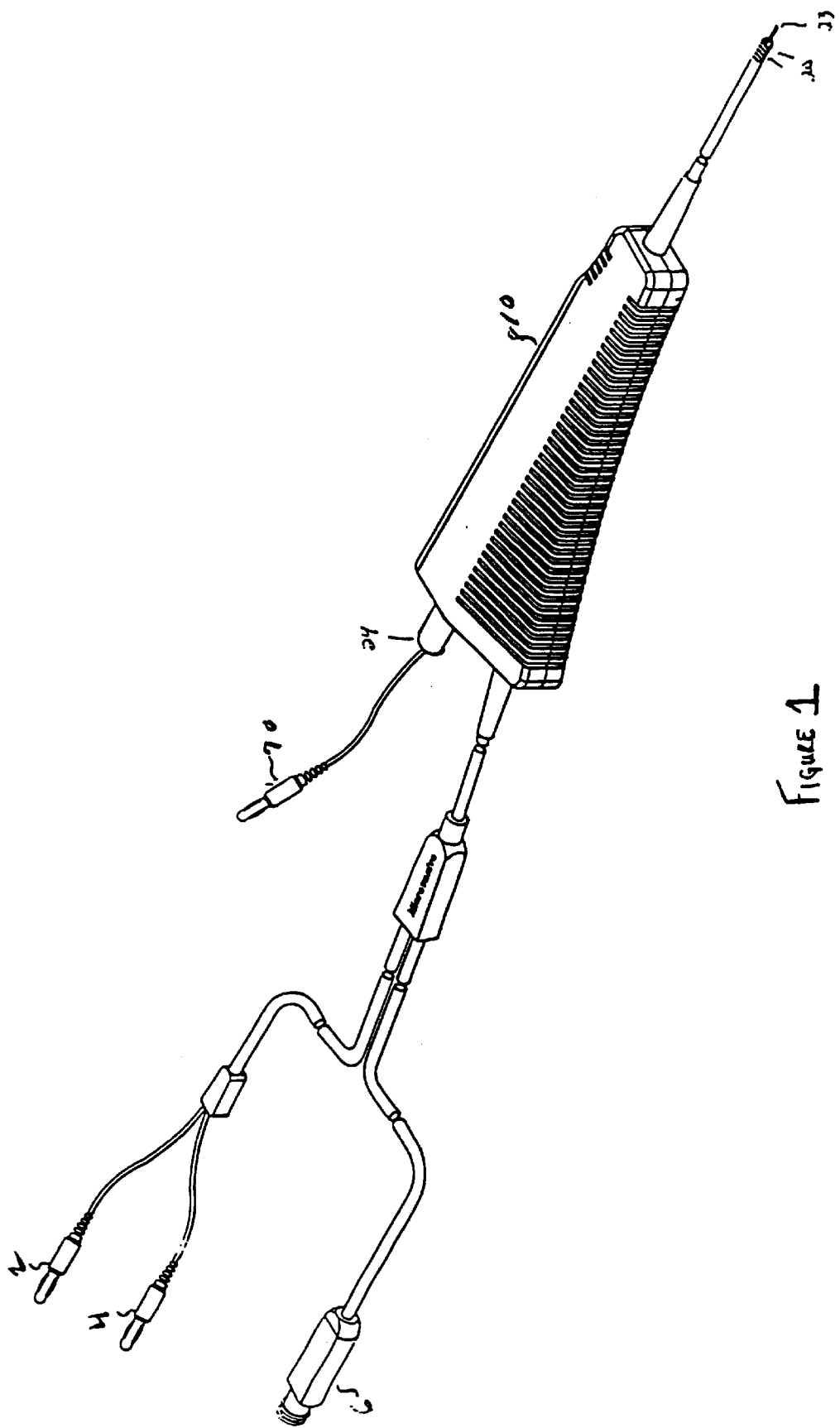
FIG. 1 is a perspective view of an integrated catheter assembly according to the present invention.

FIG. 1 shows the preferred embodiment of a electrosurgery and intervention apparatus according to the present invention, which includes a catheter assembly 10, a bipolar electrode tip 20, an electrode cutting wire 23, an operator 24, an electrical cutting wire connector 70, bipolar electrode tip connectors 2 and 4, and an irrigation hub 6.

Figure 2:
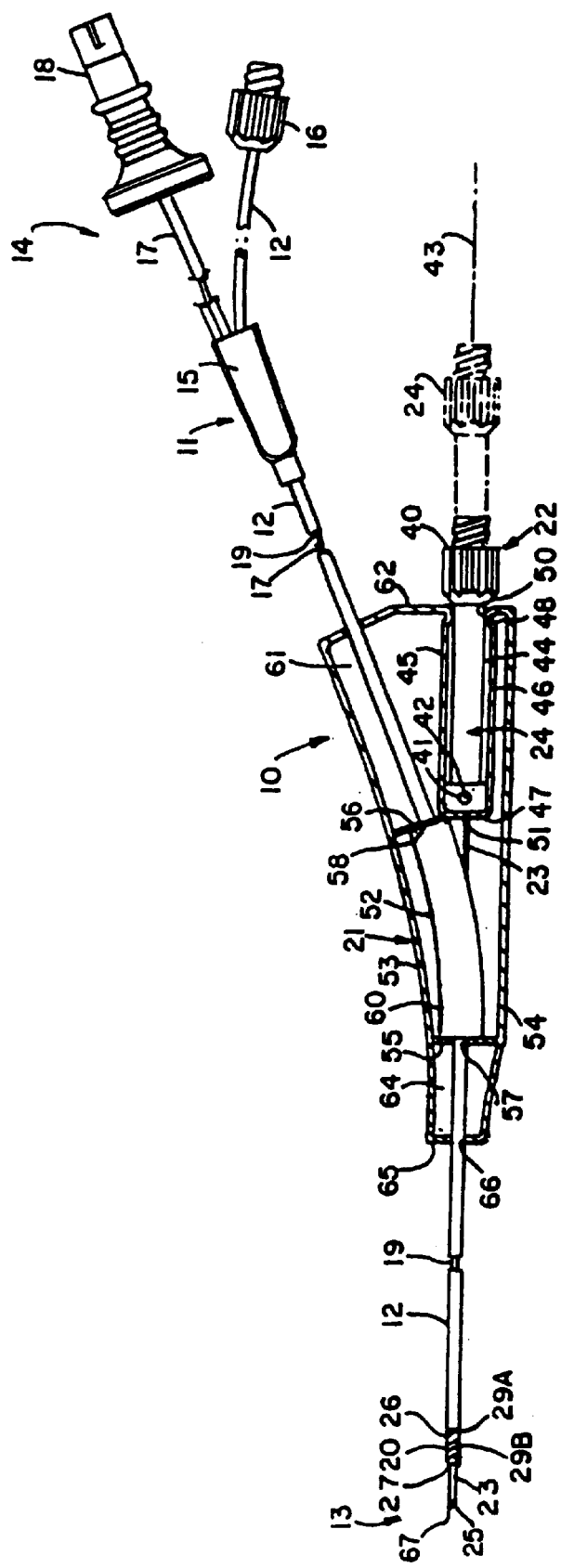
FIG. 2 is a side view, partially in section, of the integrated catheter assembly shown in FIG. 1, which assembly extends between proximal and distal end portions and includes a catheter, a cutting wire and a bipolar electrode assembly.

FIG. 2 discloses the integrated catheter assembly 10 that enables a physician to utilize diverse in situ therapy modalities at selected tissue sites without withdrawing the assembly 10 from the working channel or lumen of an endoscope. It includes a modified bipolar hemostat and irrigation system 11, such as the above identified Gold Probe™ hemostat and that described in U.S. Pat. No. 5,403,311 (incorporated herein by reference for its teachings). The system 11 enables a physician to utilize a multipurpose device for making an incision in tissue using electrosurgery, as well as for performing bipolar hemostasis and irrigation in the treatment of a bleeding vessel. The system 11 particularly includes a catheter 12 with a single lumen that extends from a distal location 13 to a proximal location 14. At the proximal location 14 a catheter hub 15 carries the catheter 12 from a Luer lock or similar catheter fitting 16 toward the distal location 13. Electrical leads 17 from an RF generator connector 18 also enter the catheter hub 15. RF generators of the type utilized with this apparatus are well known and therefore not shown. The connector 18 may be one which connects using banana type plugs. The electrical leads 17 are led into the center of the catheter 12 in the hub 15 thereby to be carried through a central lumen 19 of the catheter 12 to the distal location 13 and a bipolar electrode assembly 20. As an alternative, the catheter 12 may incorporate electrical leads in the catheter wall thereby to eliminate any contact between irrigating solutions in the lumen 19 and the electrical leads 17. The bipolar electrode assembly 20 when energized over the electrical leads 17 provides hemostatic therapy.

In accordance with this invention, a wire hub 21 directs the catheter 12 therethrough and supports the proximal end of a wire assembly 22 that includes an electrode cutting wire 23. The cutting wire 23 can move between extended and retracted positions by manipulation of an operator 24. The operator 24 is shown at its extended position in FIG. 2 by the solid lines and in its retracted position by phantom operator 24'. When the cutting wire 23 extends distally beyond the distal end of the bipolar electrode assembly 20 as shown in FIGS. 2 and 4, it can contact and penetrate tissue, enabling a physician to make surgical incisions into tissue or ablate tissue.

Referring now to different sections of the apparatus shown in FIG. 2 in more detail, FIGS. 3 and 4 depict a distal end location 13 of the integrated catheter assembly 10. In each of FIGS. 3 and 4 the distal end of the catheter 12 terminates at the bipolar electrode assembly 20. Although the electrode assembly 20 is described as bipolar, it is well understood in the art that an electrode assembly, such as the electrode assembly 20 here, can also be monopolar. The monopolar form of the electrode assembly 20 has only one of the spiral electrodes (i.e. 29A or 29B).

More specifically the bipolar electrode assembly 20 includes a cylindrical body portion 26 having a hemispherical distal end tip 27 and a proximally extending shank 28 at its other end. Discrete spiral electrodes 29A and 29B are disposed on the outer surface of the body portion 26 and the end tip 27 and connect to the electrical leads 17. A distal tip lumen 30 extends through the body portion end tip 27 and shank 28. The shank 28 is nested and supported by the catheter 12.

Still referring to FIGS. 3 and 4, a cutting wire guide portion 31 includes an end section 32 that is located in the proximal end of the lumen 30 and coextensive with a portion of the shank 28. The guide wire 31 can be, for example, located within a centerbore at the proximal end of the tip 27, or, as shown in FIGS. 3 and 4, within the lumen 30. The cutting wire guide portion 31 extends proximally from the shank 28 and constitutes a pervious guide tube for the cutting wire 23. More specifically, the cutting wire guide 31 is formed as a spring with multiple spaced turns that define inter-turn passages 33. These passages 33 allow fluid to transfer from the catheter lumen 19 and through the distal tip lumen 30 to exit from the end tip 27. Fluid flow is relatively unimpeded in the structure shown in FIG. 3 when the cutting wire 23 is retracted. The extension of the cutting wire 23 to the position shown in FIG. 4 restricts the distal tip lumen 30, but flow can still occur.

FIG. 5 depicts a preferred embodiment for the bipolar electrode assembly 20. In this particular embodiment, a tube 34 replaces the spring 31. The tube 34 has a section 35 that fits in the lumen 30 and is coextensive with a portion of the shank 28 and another section 36 that is proximal of the shank 28. This second section 36 includes a plurality of radially extending apertures 37 that act as passages for irrigation fluids from the catheter 12 through a central lumen 38.

Each of FIGS. 3 through 5 depict alternative embodiments of a bipolar electrode assembly 20 that includes first and second electrodes 29A and 29B for providing hemostatic therapy. In each embodiment a body portion 26 has a hemispherical distal end 27 and carries the electrodes 29A and 29B. A shank 28 extends proximally of the body portion 26 for insertion into the lumen 19 at the distal end of the catheter 12. A tubular pervious cutting wire guide 31 extends proximally from the shank portion 28 in the lumen 19 to be coextensive with the distal portion of the catheter 12 for supporting the distal end of the cutting wire 23 particularly in its retracted position.

Referring to FIG. 2, the operator 24 associated with the cutting wire assembly 22 includes a proximal end fitting 40 that can connect to a cutting wire electrical connector 70 (shown in FIG. 1) which enables the cutting wire 23 to be electrically charged. At its opposite end, the operator 24 includes a collar 41 and set screw 42 or other attaching apparatus for affixing the operator 24 to the cutting wire 23. Such apparatus is known in the art. In this particular embodiment the operator 24 and cutting wire 23 lie along an axis 43.

The cutting wire hub 21 can be molded or otherwise formed to include a proximal compartment 44 defined by side walls 45 and 46 and end walls 47 and 48. An aperture 50 through the end wall 48 accommodates the operator 24 while an aperture 51 at the distal end wall 47 accommodates the cutting wire 23. The end walls 47 and 48 support the proximal end of the cutting wire assembly 22 and limit the range of travel of the operator 24 along the axis 43 between the position shown in FIG. 2 wherein the collar 41 abuts the wall 47 and a retracted position in which the collar 41 abuts the end wall 50.

An intermediate compartment 52 disposed distally of the proximal compartment 44 supports the catheter 12 in a radiused orientation. Curved and straight side walls 53 and 54 of the cutting wire hub 21 and transverse end walls 55 and 56 define the compartment. The end wall 55 extends between the side wall 53 and 54; the end wall 56, between the side wall 53 and the intersection of the side wall 45 and end 47. Apertures 57 and 58 in the end walls 55 and 56 respectively capture the catheter 12.

An elastomeric seal 60 surrounds the catheter 12 and is located in the intermediate compartment 52. The cutting wire 23 penetrates the seal 60 and the wall of the catheter 12 thereby to be located in the catheter lumen 19 to extend through the distal tip 30 as shown in FIG. 3. The seal 60 prevents leakage from the catheter 12 even during axial displacement of the cutting wire 23 along the axis 43. This seal 60 generally will be formed of an elastomeric material and can take any of several forms as known in the art.

The cutting wire hub 21 includes another proximal compartment 61 adjacent the proximal compartment 44. The compartment 61 is formed by a proximal end wall 62, the side walls 45 and 53 and the end wall 57. The end walls 57 and 62 in this compartment 61 support the catheter 12 proximally of the seal 60 and, with the compartment 52 and end wall 55, provides an angular offset to the catheter 12 with respect to the axis 43.

A distal compartment 64 is formed by the side walls 53 and 54, the end wall 55 and a distal end wall 65. An aperture 66 in the end wall 65 holds the catheter 12. The end walls 55 and 65 thereby maintain the alignment of the catheter 12 along the axis 43 to facilitate the placement and containment of the cutting wire 23 within the catheter 12 lumen 19 distally of the cutting wire hub 21.

Figure 6:
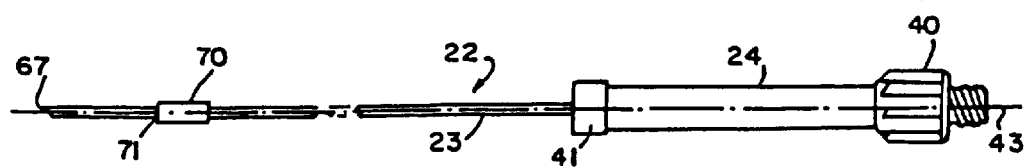
FIG. 6 is a side view of a cutting wire assembly used in the structure shown in FIGS. 2 through 4.

Still referring to FIG. 2, it is desirable to manufacture the cutting wire hub 21 as a standard unit for a variety of applications. In some applications, the limits imposed on the axial travel of the cutting wire 23 by the end walls 47 and 48 may allow an extension of the cutting wire 23 from the bipolar electrode assembly 20 that is greater than desired. It is possible to customize that extension by applying a positive stop structure to the cutting wire assembly 22. One such structure is shown in FIGS. 3, 4 and 6 where like numbers refer to like elements. As shown, particularly in FIG. 6, the cutting wire assembly 22 includes the operator 24 with its end fitting 40 and collar 41. The cutting wire 23 extends as a constant diameter wire to its distal end 67. A collar 70 having a distal, radially extending end surface 71 is located on an insulated portion of the cutting wire 23 at some predetermined location spaced from the distal end 67 by a distance that equals the length of the desired extension plus the distance between the end tip surface 27 of the bipolar electrode assembly 20 as shown in FIG. 2 and a proximal end 72 of the cutting wire guide 31 as shown in FIGS. 3 and 4.

Consequently as the cutting wire 23 moves from its retracted position in FIG. 3 to its extended position in FIG. 4, the distal end surface 71 of the collar 70, that overlies the spring 31, abuts the end 72 and prevents any further distal extension of the cutting wire 23. If the bipolar electrode assembly 20 of FIG. 5 were used, the end surface 71 would abut an end surface 73 on the tube 34.

Figure 7:
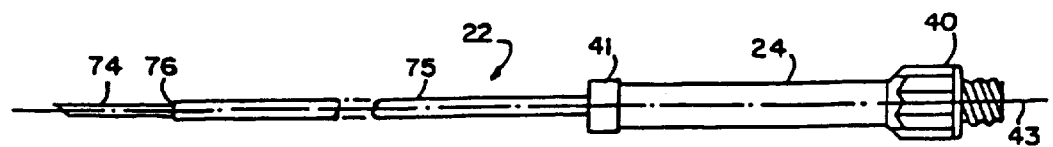
FIG. 7 is a side view of an alternate embodiment of a cutting wire assembly.
Figure 8:
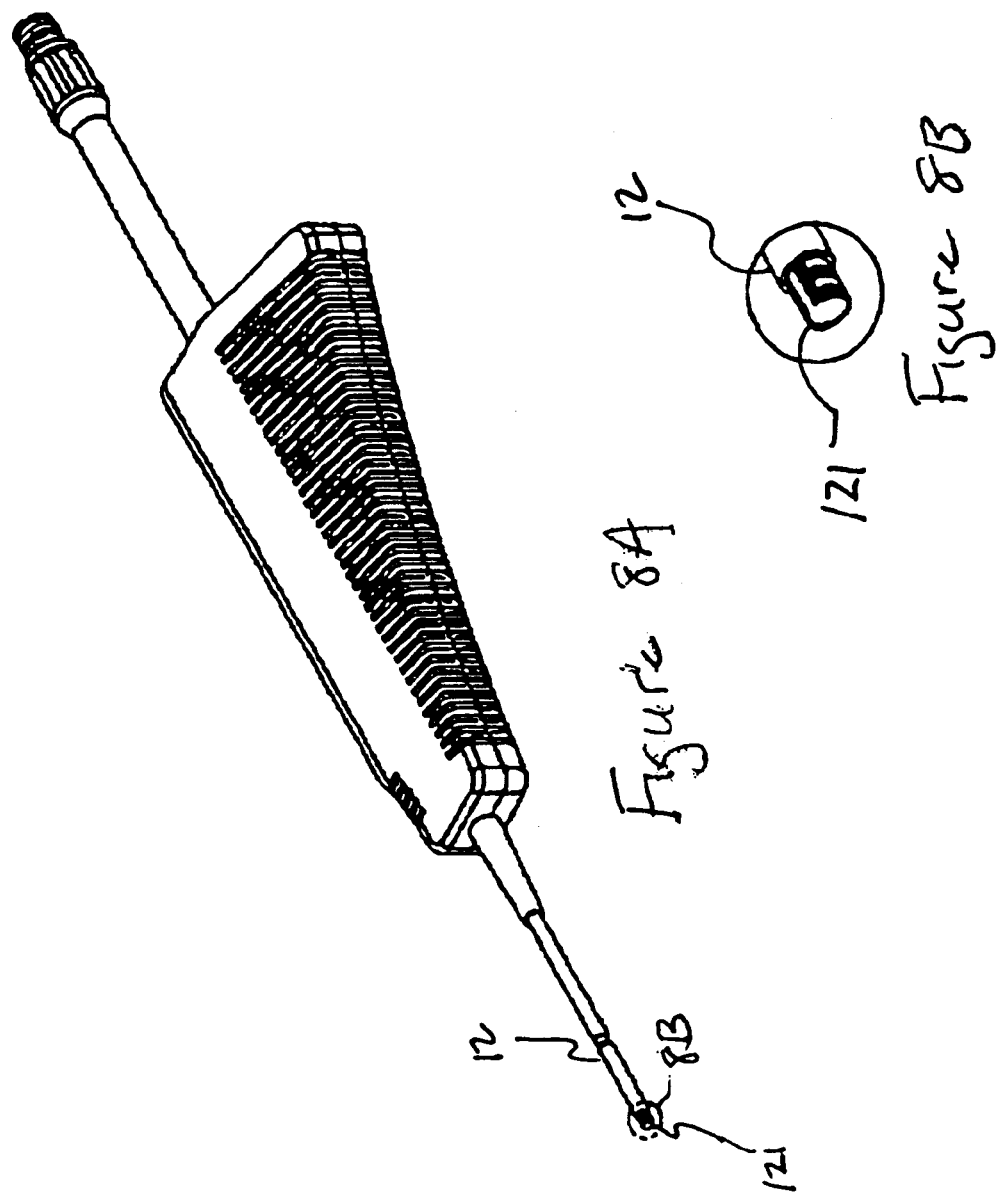
FIG. 8A is a perspective view of an exemplary integrated catheter assembly having a planar tip according to the present invention, the planar tip being in a retracted position.
FIG. 8B is an expanded perspective view of the planar tip of 8A.
Figure 9:
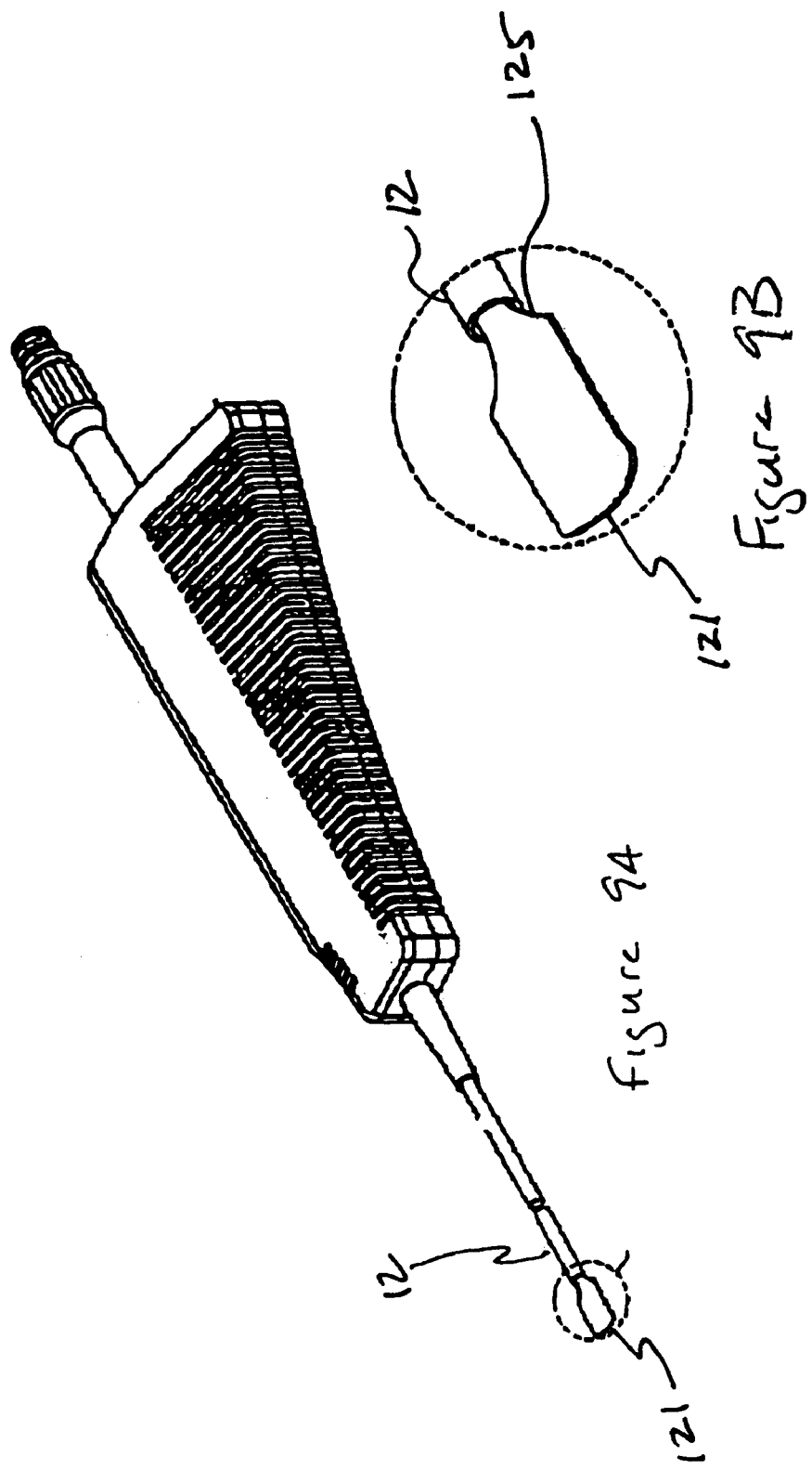
FIG. 9A is a perspective view of the assembly of FIG. 8A, with the planar tip of 8A in an extended position.
FIG. 9B is an expanded perspective view of the planar tip of 9A.

FIG. 7 discloses an alternative stop mechanism wherein the cutting wire assembly 22 includes an operator 24 with proximal end connector 40 and distal collar 41. In this embodiment the cutting wire assembly 22 comprises a distal hollow section 74 and a proximal hollow section 75. The distal section 74 has a given diameter corresponding to the diameter of the cutting wire 23 shown in FIG. 6 and determined by the application requirements. The length of the distal section 74 equals the desired extension of the cutting wire plus the distance from the distal end tip 27 to either end surface 72 of the guide 31 in FIGS. 3 and 4 or the end surface 73 of the tube 34 in FIG. 5. The proximal section 75 extends from the distal portion 74 to the operator 24 and has a larger diameter. Consequently the proximal portion 75 forms an annular radial surface 76 at its distal end that also will abut either the end 72 of the guide 31 in FIGS. 3 and 4 or the end 73 of the cutting wire guide tube 34 shown in FIG. 5.

The cutting wire 23 can be conductive along its entire length to the operator 24, or it can have conductors which are attached at a point along the length of the wire 23 that is within the lumen of the catheter 12. Additionally, all but the distal end of the cutting wire 23 can be coated or covered. Further, the wire 23 may be solid or hollow, in which case the lumen of the wire 23 can be used to allow passage of fluids for injecting. The operator 24 can have a Luer type fitting which allows passage of fluids for injecting and also have electrical leads to charge the cutting wire 23

When a physician needs to make an internal incision in a patient, the physician will, as in the prior art, insert an endoscope with a working channel. The physician can then insert the integrated catheter apparatus 10 shown in FIG. 2 through the working channel, normally with the cutting wire 23 in its retracted position (as shown in FIG. 3). If there is already internal bleeding in the area and it is necessary to irrigate the area, the physician can apply irrigating fluid through the connector 16 and the catheter lumen 19 to be ejected at the distal end tip 27 through the lumen 30 as shown in FIGS. 2 and 3. If upon viewing the site the physician decides to utilize hemostasis, it is merely necessary to position the bipolar electrode assembly 20 at the tissue and energize the electrodes 29A and 29B. The cutting wire assembly 22 has no effect on this process. If, on the other hand, the physician determines that the making an incision is appropriate before or in lieu of hemostasis, the physician can easily extend the cutting wire 23 and apply and use the cutting wire to make a surgical incision in the tissue. Thereafter the physician can irrigate the site at will and elect to use hemostasis to stem or stop any bleeding. Each of these functions can be performed without withdrawing the integrated catheter apparatus 10 from the endoscope.

It will be helpful to describe some specific embodiments of this invention for the purpose of further understanding the construction and use of this invention. Generally, the outer diameter of the catheter 12 can be as small as 5 Fr. and as large as can be accommodated by the inner diameter of an endoscopic channel. In certain specific embodiments, for example, the catheter assembly 10 can comprise a 7 Fr. or 10 Fr. catheter 12 and a 21 gauge cutting wire 23. In an another embodiment, using a cutting wire as shown in FIG. 7, the distal catheter portion comprises a 23–25 gauge tubular structure while the proximal portion comprises a 21 to 22 gauge tubular structure. In addition, one embodiment of the catheter assembly 10 in FIG. 2 extends about 220 cm. between the distal tip portion 13 and the hub 21 while the extension of the cutting wire 23 from the bipolar electrode assembly is limited to a maximum of 6 mm.

FIGS. 8A through 12 illustrate additional exemplary embodiments of a catheter assembly according to the present invention, and in particular a catheter assembly including a substantially planar tip 121. In general, the catheter assemblies illustrated in FIGS. 8A through 12 may include elements and features similar to those described above, with the addition of planar tip 121.

In an unbiased position, planar tip 121 has a substantially flat cross section, where "substantially flat" is understood to mean cross-sections which are flat and cross-sections which have a predetermined curvature (as shown in FIGS. 9A and 9B). In the same way, the term "planar tip" is used herein for convenience, and generally refers to any relatively flat or laterally compressed surface, regardless of thickness and regardless of whether the surface defines a plane or has a predetermined curvature.

Generally, planar tip 121 is formed of any suitable material, but preferable one that is flexible so that, as shown in FIGS. 8A and 8B, planar tip 121 may be inserted into and through a catheter 12. In this position, planar tip 121 has a substantially circular cross section, as shown in FIG. 8B. This arrangement allows planar tip 121 to bend if necessary, to facilitate navigation to an operative position.

Once placed in an operative position, a cutting assembly which may include a shaft or wire 23 can be extended to place planar tip 121 into an extended position clear of catheter 12. Once planar tip 121 exits the distal end of catheter 12, it may assume its unbiased, substantially flat configuration illustrated in FIGS. 9A and 9B. In this configuration, planar tip 121 may be used as a cutting blade, or may be used as an electrocautery device, desiccation device, or ablation device (or any suitable combination thereof), as described herein.

Preferably planar tip 121 includes an electrode, which may be formed on a face of planar tip 121 by circuitry. In the illustrated embodiment of FIG. 10, planar tip 121 includes a bipolar electrode formed by two circuits 123a and 123b. Alternatively, planar tip 121 may include a monopole electrode as known in the art. When formed as a bipolar electrode, circuits 123a, 123b may be in any suitable pattern. Preferably planar tip 121 is constructed of non-conductive materials, or includes a face or coating of non-conductive materials, to separate circuits 123a, 123b. Circuits 123a and 123b may be connect to electrical conduits within catheter 12, as described above.

Figure 10:
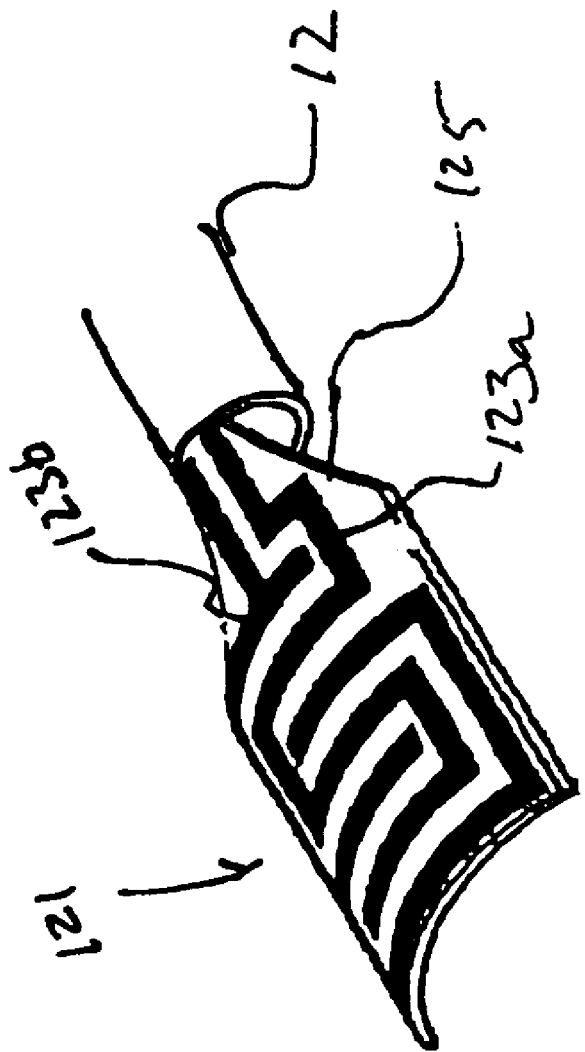
FIG. 10 is a perspective view of an exemplary planar tip according to the present invention.

As also illustrated in FIG. 10, planar tip 121 preferably includes a tapered base 125, which may be connected to shaft or wire 23. Tapered base 125 assists planar tip 121 in "rolling" back to a retracted position within catheter 12. In this retracted position, planar tip 121 may have a generally circular cross section. It should also be noted that while the planar tip 121 illustrated herein is generally rectangular in shape (apart from tapered base 125), planar tip 121 may be any suitable shape, for example circular, oval, or ovoid.

Figure 11:
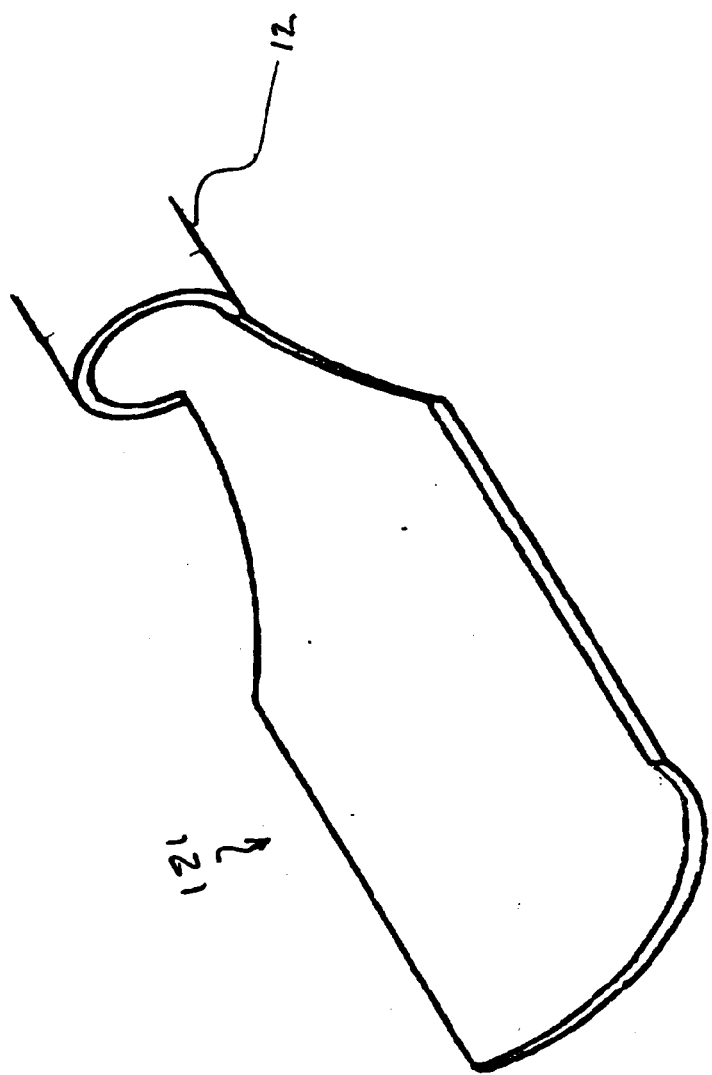
FIG. 11 is a perspective view of a further exemplary planer tip according to the present invention.
Figure 12:
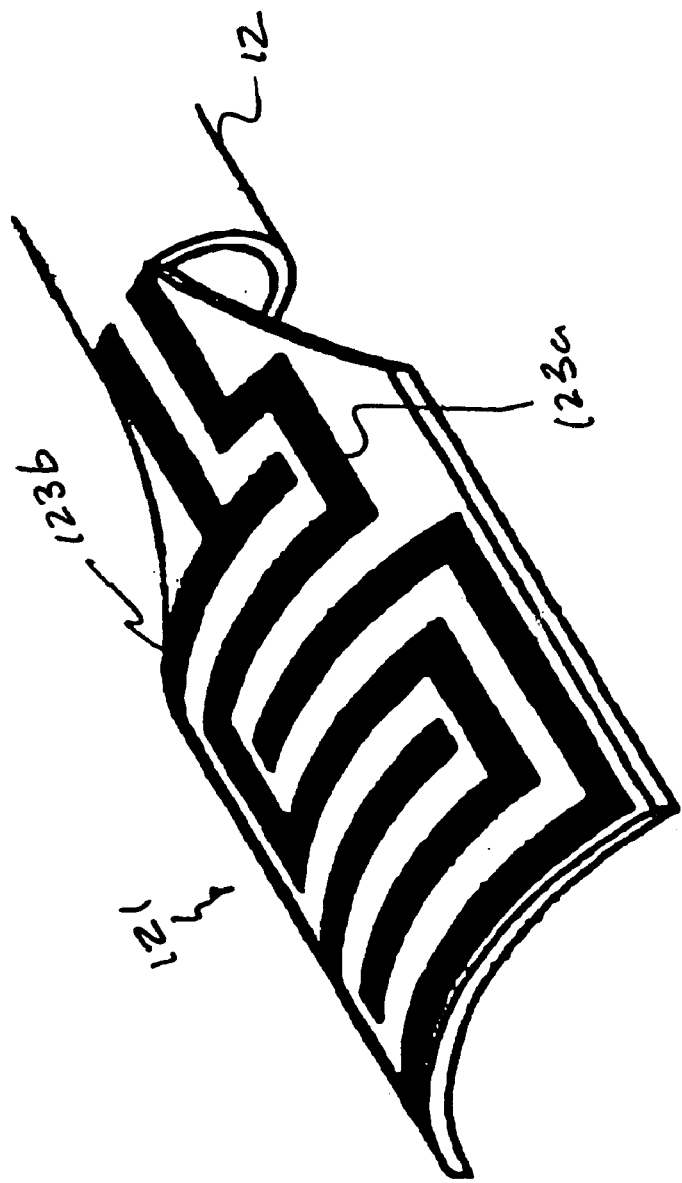
FIG. 12 is another perspective view of the planar tip of FIG. 11.

FIGS. 11 and 12 illustrate an additional exemplary embodiment of a planar tip 121 according to the present invention. In this embodiment, planar tip 121 is fixed relative to the distal end of catheter 12, rather than movable with respect to catheter 12. In this embodiment, catheter 12 with planar tip 121 may be introduced as a unit, for example through an endoscope.

Although this invention has been described in terms of a specific embodiment, and certain modifications, still other modifications can be made. For example, cutting wire assembly 22 can comprise a one-piece metal structure in the form shown in FIG. 6. In the form shown in FIG. 7 the distal portion might be constructed of a metal while the proximal portion 75 also may include means for preventing rotation about the axis 43 during use. Thus it will be apparent that these and other modifications can be made to the disclosed apparatus without departing from the invention.

What is claimed is:

1. A planar tip for a catheter assembly, comprising:
   a substantially planar surface having first and second faces;
   an electrode disposed on the first face;
   means for unrolling the planar tip when it is extended; and
   means for rolling planar tip back up when it is retracted;
   wherein when the planar tip is in a retracted, biased position, the planar tip has a rolled configuration having a substantially curved cross section, and when the planar tip is in an extended, unbiased position, the planar tip has an unrolled configuration having a substantially flat cross section;
   wherein the means for unrolling the planar tip when it is extended comprises the elasticity of the planar tip.

2. The planar tip according to claim 1, wherein when the planar tip is in an extended, unbiased position, the planar tip has a slightly curved cross section.

3. The planar tip according to claim 2, wherein the electrode is a bipolar electrode formed by first and second circuits disposed on the first face, the first and second circuits being separated by a non-conductive portion of the planar surface.

4. The planar tip according to claim 1, wherein when the planar tip is in an extended, unbiased position, the planar tip has a flat cross section.

5. The planar tip according to claim 4, wherein the electrode is a bipolar electrode formed by first and second circuits disposed on the first face, the first and second circuits being separated by a non-conductive portion of the planar surface.

6. A planar tip for a catheter assembly, comprising:
   a substantially planar surface having first and second faces;
   an electrode disposed on the first face;
   means for unrolling the planar tip when it is extended; and
   means for rolling planar tip back up when it is retracted;
   wherein when the planar tip is in a retracted, biased position, the planar tip has a rolled configuration having a substantially curved cross section, and when the planar tip is in an extended, unbiased position, the planar tip has an unrolled configuration having a substantially flat cross section;

wherein the means for rolling the planar tip back up when it is retracted comprises a tapered base of the planar tip.

7. The planar tip according to claim 6, wherein when the planar tip is in an extended, unbiased position, the planar tip has a slightly curved cross section.

8. The planar tip according to claim 7, wherein the electrode is a bipolar electrode formed by first and second circuits disposed on the first face, the first and second circuits being separated by a non-conductive portion of the planar surface.

9. The planar tip according to claim 6, wherein when the planar tip is in an extended, unbiased position, the planar tip has a flat cross section.

10. The planar tip according to claim 9, wherein the electrode is a bipolar electrode formed by first and second circuits disposed on the first face, the first and second circuits being separated by a non-conductive portion of the planar surface.

* * * * *